(12) United States Patent
Baccelli et al.

(10) Patent No.: US 6,454,805 B1
(45) Date of Patent: Sep. 24, 2002

(54) INTERBODY CAVITY IMPLANT, IN PARTICULAR FOR CERVICAL VERTEBRAE

(75) Inventors: Christian Baccelli, Ayguemorte les Graves; Frédéric Conchy, Saint Médard d'Eyrans, both of (FR)

(73) Assignee: DIMSO (Distribution Medicale du Sud-Ouest) (FR)

( * ) Notice: Subject to any disclaimer, the term of this patent is extended or adjusted under 35 U.S.C. 154(b) by 0 days.

(21) Appl. No.: 09/786,179
(22) PCT Filed: Sep. 3, 1999
(86) PCT No.: PCT/FR99/02107
§ 371 (c)(1), (2), (4) Date: Jul. 11, 2001
(87) PCT Pub. No.: WO00/13618
PCT Pub. Date: Mar. 16, 2000

(30) Foreign Application Priority Data

Sep. 4, 1998 (FR) .............................................. 99 11175

(51) Int. Cl.[7] .................................................. A61F 2/44
(52) U.S. Cl. .................................. 623/17.11; 623/17.13; 623/17.15
(58) Field of Search .......................... 623/17.11, 17.15, 623/17.16, 17.12, 17.13, 16.11, 23.61; 606/61, 60

(56) References Cited

U.S. PATENT DOCUMENTS

| | | | | |
|---|---|---|---|---|
| 5,236,460 | A | * | 8/1993 | Barber |
| 5,609,635 | A | * | 3/1997 | Michelson |
| 5,800,550 | A | * | 9/1998 | Sertich |
| 6,296,664 | B1 | * | 10/2001 | Middleton |

* cited by examiner

Primary Examiner—Pedro Philogene
(74) Attorney, Agent, or Firm—Lerner, David, Littenberg, Krumholz & Mentlik, LLP

(57) ABSTRACT

The invention concerns an implant comprising a body with an upper surface and a lower surface capable of pressing on the vertebral end-plate located immediately above and beneath and having further at least a through aperture emerging on the upper and lower surfaces. The invention is characterized in that the implant further comprises an anchoring member mounted in such a way as to be capable of moving in the aperture. The said anchoring member includes a support part adjacent to a first vertebral end-plate, and at least a projecting anchoring element extending from the support part towards the opposite vertebral end-plate. Thus, when the implant is compressed between the vertebral end-plates, the anchoring member is stressed by the first vertebral end-plate at the support part to move relative to the body and the at least providing projecting element overlaps the body surface facing the opposite vertebral end-plate and is anchored therein. The invention is particularly applicable to bone fusion between cervical vertebrae.

18 Claims, 1 Drawing Sheet

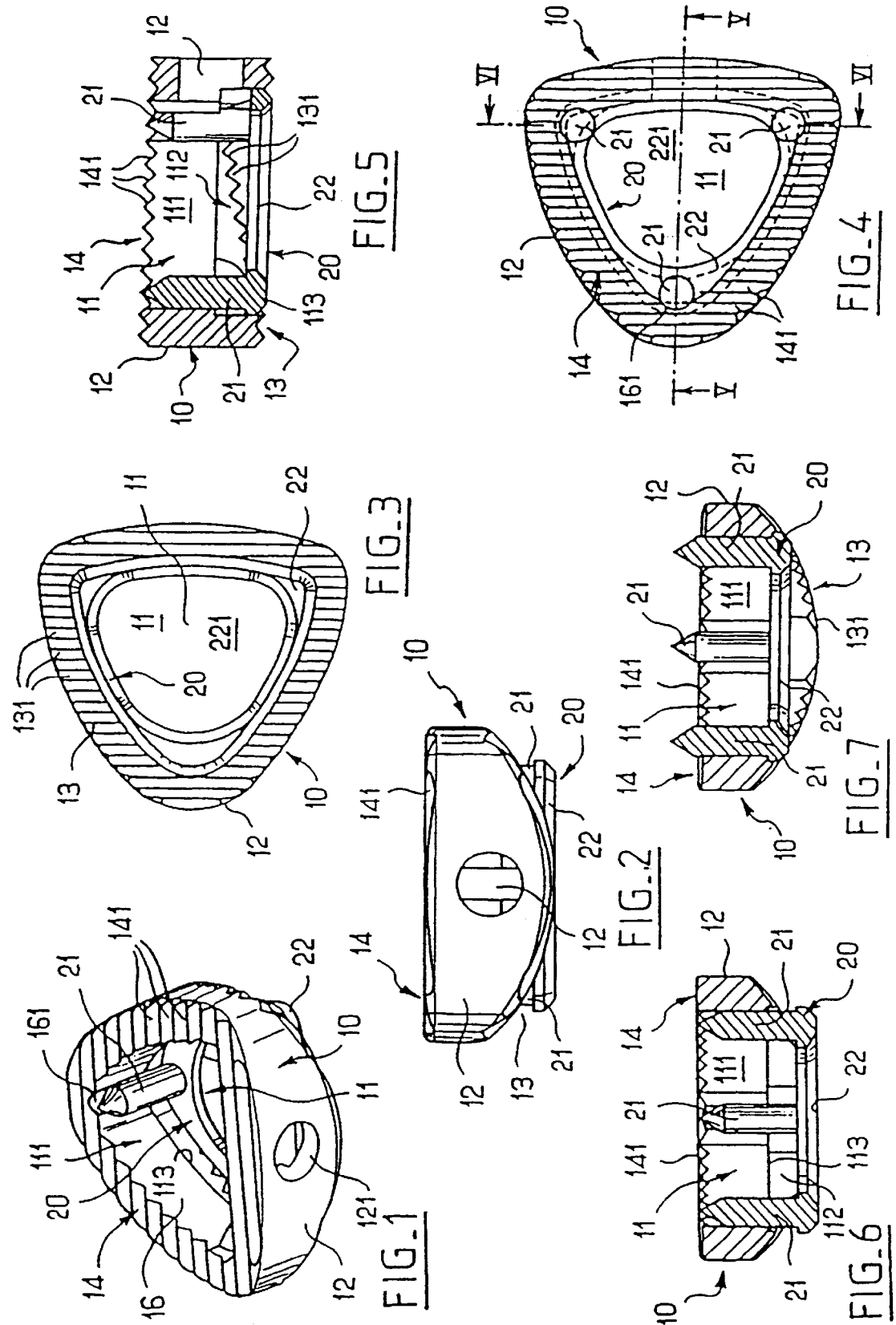

INTERBODY CAVITY IMPLANT, IN PARTICULAR FOR CERVICAL VERTEBRAE

The present invention relates in a general manner to interbody cages intended to partially or completely replace an intervertebral disc in surgical treatment of the spine and to permit bone fusion between the overlying and underlying vertebral plates.

A number of types of interbody cages are already known in the prior art. One cage which is particularly widely used is made up of a one-piece body made of biocompatible material such as a titanium alloy or a stainless steel, of which the upper surface and the lower surface have reliefs such as serrations of triangular cross section which are intended to provide anchoring in the overlying and underlying vertebral plates when the distraction effected between the vertebrae for the purpose of fitting the implant is released. Such a cage is also provided with at least one opening which passes through the body from top to bottom and opens out on its upper and lower faces. The cavity constituted by this opening is filled with an osteogenic material or bone graft so as to ensure bone growth through it between the vertebral plates and, in the long term, rigid bone fusion between these plates.

However, these known cages have certain limitations, particularly in terms of the stability of the anchoring in the vertebral plates over time, which stability is essential in order to achieve bone fusion.

These cages are also poorly adapted to the cervical vertebrae, where the incurved configuration of the vertebral plates can render the principle of this anchoring by serrations insufficient per se.

The present invention aims to overcome these limitations of the prior art and to propose a novel implant of the interbody cage type which is well adapted to implantation in the region of the cervical vertebrae and which is able to be joined to the vertebral plates with an excellent quality of anchoring.

Another object of the invention is to propose an implant of the interbody cage type whose fitting is particularly simple and whose weight can be reduced compared with the entirely metal cages of the prior art, and whose manufacture can therefore be made simpler and less expensive.

Thus, the invention proposes an implant of the interbody cage type, particularly for cervical vertebrae, comprising a body which has an upper face and a lower face, which are able to bear on the overlying and underlying vertebral plates, and which also comprises at least one through-opening which opens out on the said upper and lower faces, characterized in that it additionally comprises an anchoring member mounted in such a way as to be able to move in the said opening, the said anchoring member comprising a bearing part adjacent to a first vertebral plate, and at least one projecting anchoring element extending from the said bearing part in the direction of the opposite vertebral plate, such that when the implant is compressed between the vertebral plates, the said anchoring member is stressed by the first vertebral plate in the area of the said bearing part so as to move in relation to the body and so that the said projecting element at least provided juts out from that face of the body turned toward the opposite vertebral plate and anchors in the latter.

Preferred but nonlimiting features of the implant according to the invention are as follows:

the body has, on at least one of its upper and lower faces, complementary anchoring arrangements, the said anchoring member has a plurality of projecting elements, the said projecting elements are elongate and essentially parallel to one another, the projecting anchoring element or each projecting anchoring element has the form of a rod with a pointed free end, the said opening of the body has a bearing arrangement for the said anchoring member in order to limit the course of movement of the latter caused by the said first vertebral plate, the said arrangement consists of a shoulder between two parts of different sizes of the said opening, the said bearing part of the anchoring member fits tightly into the larger-sized part of the said opening, when the anchoring member bears against the bearing arrangement, the bearing part of the said member is entirely inscribed within the lower face of the body, the anchoring member has a plurality of projecting anchoring elements all fitting tightly into the smaller-sized part of the said opening, the said bearing part of the anchoring member has the form of a ring in which a central opening ensures continuity of passage between the upper and lower faces of the body, through the said opening of the body, the body has a generally rounded external form, with zones of greater curvature and zones of lesser curvature, the said opening of the body has a contour with a form similar to the said outer form of the body, the anchoring member is provided with a plurality of projecting elements situated in the vicinity of zones of greater curvature of the said opening and received in recesses formed in these zones, one of the upper and lower faces of the body is convex, the bearing part of the anchoring member is generally plane, the body is made of a biocompatible polymer material such as polyetherether ketone, the anchoring member is made of a biocompatible metal alloy.

Other features, aims and advantages of the present invention will become clearer on reading the following detailed description of a preferred embodiment thereof, given as a nonlimiting example and with reference to the attached drawings, in which:

FIG. 1 is a perspective view of an implant according to the invention,

FIG. 2 is a front elevation view of the implant in FIG. 1,

FIG. 3 is a bottom view of the implant in FIGS. 1 and 2,

FIG. 4 is a top view of the implant in FIGS. 1 to 3,

FIG. 5 is a longitudinal sectional view along the line V—V in FIG. 4,

FIG. 6 is a transverse sectional view along the line VI—VI in FIG. 4, in a first position of the implant, and FIG. 7 is a view analogous to FIG. 6, in a second position of the implant.

Referring now to the drawing, an implant has been shown which is intended to form an interbody cage between two vertebral plates, preferably in the area of the cervical vertebrae, and which is made up of two parts, namely an outer cage body 10 and an inner reinforcement 20.

The cage body has in this case, seen from above, a generally triangular contour with rounded corners. Other contours, preferably all with rounded corners, can also be adopted.

The body 10 has a generally plane upper face 14 provided with serrations 141 of triangular cross section, extending in a direction essentially perpendicular to the direction of fitting between the vertebral plates, and intended to participate in the anchoring in the overlying vertebral plate.

The lower face 13 of the body has for its part a convexity which is adapted to be essentially complementary to the natural concavity of the upper face of the underlying cervical vertebral plate. This lower face 13 also has serrations 131 providing the anchoring in the said underlying vertebral plate.

Extending between the upper and lower faces is a generally smooth peripheral face 12, in a front region of which there is an opening 121, preferably provided with a thread, the latter allowing the implant to be mounted at the end of an instrument, of a type conventional per se.

The body 10 is passed through by a cavity 11 which opens out on its upper face and on its lower face, this cavity being made up of an upper part 111 and a lower part 112 which is slightly wider than the upper part, so as to define a shoulder 113 at the transition between these parts, for reasons explained below.

It will be observed that the wall 16 defining the cavity 11 has the same form as the outer contour of the body 10, here generally triangular with rounded corners.

The reinforcement 20 is made up of a component which is designed to be able to be received inside the cavity 11. This reinforcement has at its base a ring 22 which extends in a generally horizontal plane and whose outer contour substantially matches, over at least a substantial part of its length, the shape of the wall of the lower part 112 of the cavity 11 of the body 10, in such a way as to be able to be guided in vertical translation in the said lower part. This ring is passed through by a central opening 221.

Extending upward from the ring in this case there are three spikes 21 in the form of cylindrical rods whose upper end is conical in order to form a point directed upward. These spikes preferably extend from the three regions of the ring corresponding to the three "corners" of the rounded triangle formed by the cavity 11 of the body 10 and are positioned in such a way as to extend substantially along the inner wall defining the narrower top part 111 of the said cavity, so as to also form a guide for the said vertical translation.

In particular, the spikes 21 are here arranged level with the outer edge of the ring 22, while the wall 16 in the area of the upper part 111 of the cavity has locally, in the area of the spikes 21, shallow recesses 161 intended to form cradles for the respective spikes ensuring the abovementioned guiding.

It will be observed here that despite the presence of the reinforcement 20, the central opening 221 of the ring makes it possible to conserve the continuity of passage between the upper face and the lower face of the body 10, as defined by its cavity 11.

The implant is fitted by placing the reinforcement 20 in the body 10 in the position illustrated in FIGS. 2 and 6, that is to say in such a way that the spikes 21 are set slightly back from or are flush with the upper face 14 of the body 10.

The internal space of the implant defined by the cavity 11 is filled partly or completely with bone graft or an osteogenic substance. The distraction between the cervical vertebral plates being effected with the aid of instrumentation which is conventional per se, the implant is placed between these plates. By releasing the distraction, the implant is compressed between the plates, and the lower plate, which it will be recalled has a natural concavity, stresses the reinforcement 20 upward by acting on the area of the ring 22, the flatness of which means that at the moment of fitting, some of its regions jut downward from the convex lower face 13 of the body. By exerting this pressure, the lower vertebral plate pushes the reinforcement 20 upward so as to cause the spikes 21 to jut upward beyond the upper face 14 of the body (see FIG. 7), and the pointed ends of these spikes penetrate the upper vertebral plate in order thereby to ensure particularly effective anchoring. The serrations 131, 141 for their part ensure secondary anchoring, which completes the main anchoring realized by the spikes 21.

It will be observed here that the stop formed by the shoulder 113 makes it possible to limit the movement of the reinforcement 20 upward, and thus to effectively control the degree of penetration of the spikes in the upper vertebral plate, given that excessive penetration risks weakening the vertebral body.

It will also be observed that in this stop position, as illustrated in FIG. 7, the ring 22 of the reinforcement 2 is substantially in a position flush with the lower face 13 of the body 10, so that the body bears against the lower vertebral plate under good conditions over the maximum surface area.

Having read the above, it will be appreciated that the reinforcement 20, by virtue of its shape being complementary with the inside of the body 10, fulfills a function of reinforcing this body. It is thus particularly advantageous to form the reinforcement 20 using a biocompatible metal alloy such as a titanium alloy or a stainless steel, while the body 10 can be made of a biocompatible polymer such as polyetherether ketone, without compromising the strength of the implant.

An implant is thus obtained which is lighter and which is easier and more economical to produce, given that the body 10 can be produced by molding.

In addition, since the polymer is radiotransparent, the fact that the reinforcement 20 is metal permits post-surgical verification of the stability of the implant by means of radiography.

Thus, the reinforcement 20 has in this case three main functions, namely a main anchoring function, a function of reinforcement of the body and a function of radiographic monitoring.

Of course it is possible to adapt the number and arrangement of the spikes 21, and likewise the size and shape of the cavity of the body 10 which accommodates this reinforcement. However, it is preferable, in order to ensure stable bone fusion, for the horizontal section of the cavity 11 to occupy at least a quarter of the overall horizontal section of the implant.

What is claimed is:

1. An implant of the interbody cage type, particularly for cervical vertebrae, comprising a body which has an upper face and a lower face, which faces are able to bear on the overlying and underlying vertebral plates, and having at least one through-opening which opens out on said upper and lower faces, and additionally comprises an anchoring member movably mounted in said opening, said anchoring member comprising a bearing part adjacent to a first vertebral plate, and at least one projecting anchoring element extending from the said bearing part in the direction of the opposite vertebral plate, such that when the implant is compressed between the vertebral plates, said anchoring member is stressed by the first vertebral plate in the area of the said bearing part so as to move in relation to the body and so that said at least one projecting anchoring element juts out from that face of the body turned toward the opposite vertebral plate and anchors in the latter.

2. The implant according to claim 1, wherein the body has, on at least one of its upper and lower faces, complementary anchoring elements.

3. The implant according to claim 1, wherein said anchoring member has a plurality of projecting anchoring elements.

4. The implant according to claim 3, wherein said projecting anchoring elements are elongate and essentially parallel to one another.

5. The implant according to claim 1, wherein the projecting anchoring element or each projecting anchoring element has the form of a rod with a pointed free end.

6. The implant according to claim 1, wherein said opening of the body has a bearing arrangement for said anchoring member in order to limit the course of movement of the latter caused by the said first vertebral plate.

7. The implant according to claim 6, wherein said bearing arrangement consists of a shoulder between two parts of different size of said opening.

8. The implant according to claim 7, wherein said bearing part of the anchoring member fits tightly into a larger-sized part of said opening.

9. The implant according to claim 6, wherein when the anchoring member bears against the bearing arrangement, the bearing part of the said member is entirely inscribed within the lower face of the body.

10. The implant according to claim 7, wherein the anchoring member has a plurality of projecting anchoring elements all fitting tightly into a smaller-sized part of the said opening.

11. The implant according to claim 1, wherein said bearing part of the anchoring member has the form of a ring in which a central opening ensures continuity of passage between the upper and lower faces of the body, through said opening of the body.

12. The implant according to claim 1, wherein the body has a generally rounded external form, with zones of greater curvature and zones of lesser curvature.

13. The implant according to claim 12, wherein said opening of the body has a contour with a form similar to said external form of the body.

14. The implant according to claim 13, wherein the anchoring member is provided with a plurality of projecting elements situated in the vicinity of zones of greater curvature of said opening and received in recesses formed in these zones.

15. The implant according to claim 1, wherein one of the upper and lower faces of the body is convex.

16. The implant according to claim 15, wherein the bearing part of the anchoring member is generally planar.

17. The implant according to claim 1, wherein the body is made of a biocompatible polymer material such as polyetherether ketone.

18. The implant according to claim 1, wherein the anchoring member is made of a biocompatible metal alloy.

* * * * *

UNITED STATES PATENT AND TRADEMARK OFFICE
CERTIFICATE OF CORRECTION

PATENT NO.     : 6,454,805 B1                                    Page 1 of 1
DATED          : September 24, 2002
INVENTOR(S)    : Christian Baccelli and Frédéric Conchy It is certified that error appears in the above-identified patent and that said Letters Patent is hereby corrected as shown below:

<u>Column 1,</u>
Line 4, insert -- BACKGROUND OF THE INVENTION --.
Line 32, insert -- SUMMARY OF THE INVENTION --.

<u>Column 2,</u>
Line 41, insert -- BRIEF DESCRIPTION OF THE DRAWINGS --.
Line 57, insert -- DESCRIPTION OF THE PREFERRED EMBODIMENTS --.

<u>Column 4,</u>
Line 47, insert -- Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. --

Signed and Sealed this

Fourth Day of February, 2003

JAMES E. ROGAN
*Director of the United States Patent and Trademark Office*